United States Patent [19]

Higgins et al.

[11] Patent Number: 4,696,298
[45] Date of Patent: Sep. 29, 1987

[54] VITRECTOMY CUTTING MECHANISM

[75] Inventors: Daniel E. Higgins, St. Louis; James C. Easley, Fenton, both of Mo.

[73] Assignee: Storz Instrument Company, St. Louis, Mo.

[21] Appl. No.: 799,748

[22] Filed: Nov. 19, 1985

[51] Int. Cl.[4] .............................................. A61B 17/32
[52] U.S. Cl. ....................................... 128/305; 604/22
[58] Field of Search ............ 128/305, 329 R, 751–755; 604/22; 30/241

[56] References Cited

U.S. PATENT DOCUMENTS

| | | | |
|---|---|---|---|
| 3,815,604 | 6/1974 | O'Malley et al. | 128/305 |
| 3,884,238 | 5/1975 | O'Malley et al. | 128/305 |
| 3,994,297 | 11/1976 | Kopf | 128/305 |
| 4,011,869 | 3/1977 | Seiler, Jr. | 128/305 |
| 4,111,207 | 9/1978 | Seiler, Jr. | 128/305 |
| 4,200,106 | 4/1980 | Douvas et al. | 128/305 |
| 4,314,560 | 2/1982 | Helfgott et al. | 128/305 |
| 4,530,359 | 7/1985 | Helfgott et al. | 128/329 R |
| 4,601,290 | 7/1986 | Effron et al. | 128/305 |

Primary Examiner—Richard J. Apley
Assistant Examiner—H. Macey
Attorney, Agent, or Firm—Harness, Dickey & Pierce

[57] ABSTRACT

An improved vitrectomy probe for removing vitreous and cutting mechanism therefore. A hollow elliptically flared cutting blade is reciprocated within a smooth-bore hollow needle of a microsurgical vitrectomy probe across a cutting edge of the outer needle slicing the fibrous material of the vitreous. The cutting blade is configured to provide a more even contact of the cutting surfaces as the cutting blade is reciprocated across the cutting edge of the probe needle. A pressurized fluid source, diaphragm and spring cooperate to provide for the reciprocation of the blade.

16 Claims, 7 Drawing Figures

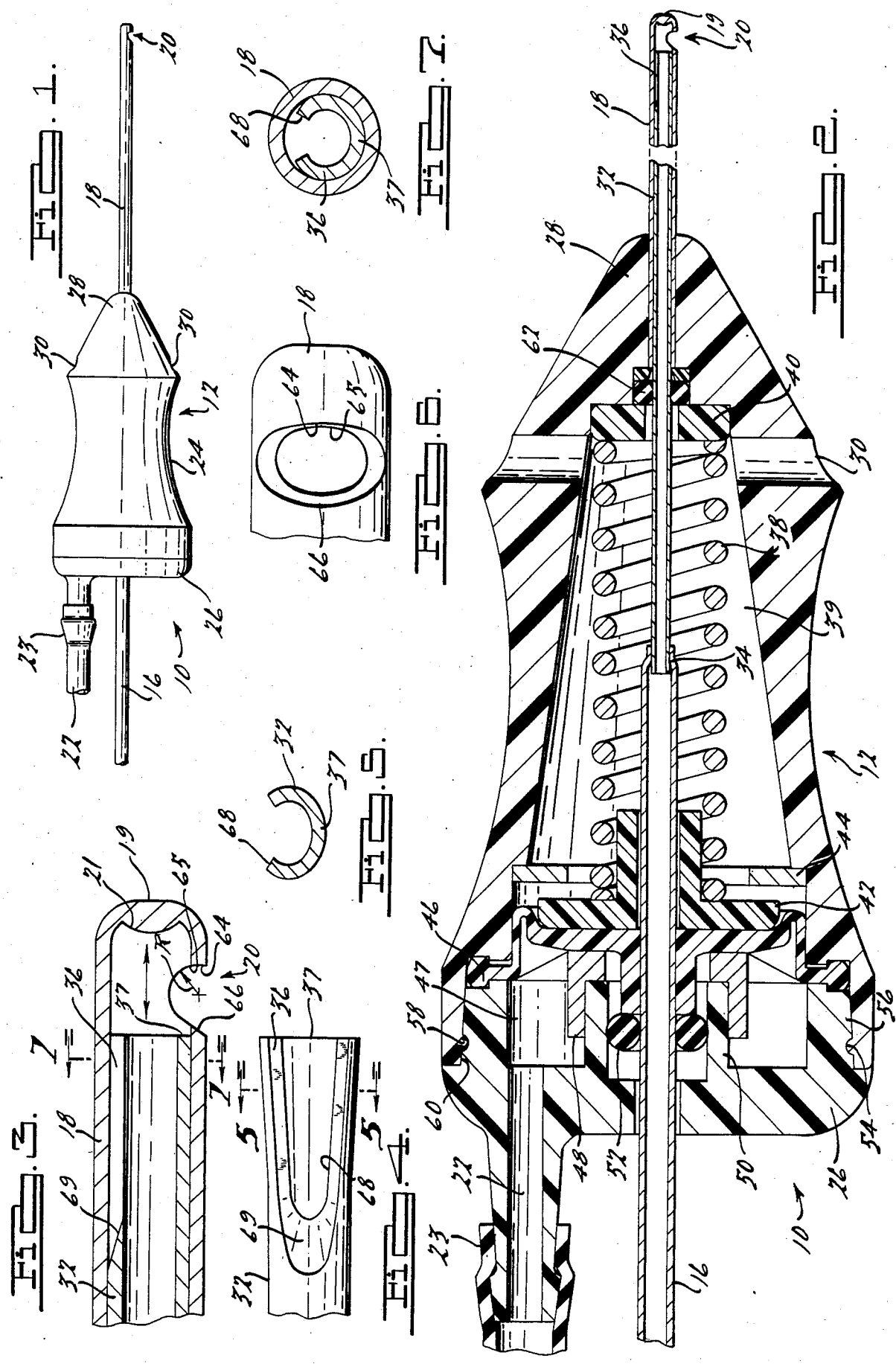

VITRECTOMY CUTTING MECHANISM

BACKGROUND OF THE INVENTION

The present invention relates to improved surgical instruments for use in ophthalmic surgery, particularly microsurgical cutting probes used to remove the vitreous from an eye.

There are ophthalmic surgical procedures which require the removal of all or a part of the vitreous humor in the eye. The vitreous humor (or "vitreous") is a colorless transparent jelly-like material that fills the area of the eye posterior to the crystalline lens. The vitreous is filled with numerous fiber-like materials which are often attached to the retina. Removal of the vitreous is difficult due to the presence of the fibers and the possibility of detachment of the inflexible and very delicate retina.

The present invention provides an improved microsurgical cutting instrument with an elongated needle or probe which is adapted to cut the fibers within the vitreous and remove the vitreous from the eye. The vitreous is removed primarily through the use of a suction through the hollow probe needle which is inserted through an incision in the eye, under the direction of a surgeon using a microscope. A unique and advantageous cutting mechanism is contained at the outer end of the probe needle and cuts the fibrous material as the vitreous is being aspirated through the needle.

During ophthalmic microsurgery, several surgical probes and instruments are used, such as cutting tools and irrigation/aspiration instruments. The surgical systems also contain a switch or switches (usually foot activated switches operated by the surgeon) controlling the suction and liquid flow and a remote base unit which houses the suction and pumping mechanisms and containers for storing irrigation liquid and collected material. The ophthalmic surgeon controls the positioning and functioning of the instruments in the eye through the use of a microscope.

The basic concept and operation of a vitrectomy probe combines a constant suction with a repeated cutting motion of a blade. The probe comprises a stationary outer needle which contains one or more apertures to receive the vitreous when suction is applied. A cutting blade located within the outer needle cuts the fibers of the vitreous as it is drawn into the needle. Various types of cutting mechanisms are known today including rotating or reciprocating blades.

Since some of the fibers contained within the vitreous are attached to the retina, any incomplete cutting of the fibers could create retinal traction which could lead to retinal detachment. Incomplete cutting may result from a dull cutting blade, wherein the blade would merely pull the fibers and increase the retinal traction, or from a poor interface of the cutting edges of the outer needle and the cutting blade wherein the shearing effect of the edges passing across one another is reduced. In addition, imperfect alignment of the cutting blade within the outer tube would cause the shearing action to be localized at the center of the cutting edges and prevent the outer portions of the cutting edges from interfacing sufficiently close enough for a clean shearing action to occur.

SUMMARY OF THE INVENTION

The present invention comprises a microsurgical probe instrument which comprises an outer needle with a substantially smooth inner bore containing a round, beveled aperture or port leading up to a cutting edge and a hollow tubular member having a cutting blade on one end which is reciprocated within the outer needle. The blade is flared into an elliptical shape and the shearing effect of reciprocating the cutting blade past the cutting edge of the probe needle is improved.

The tubular member containing the blade reciprocates inside the outer tube across the aperture in a shearing or scissors-like action, slicing the fibrous portion of the vitreous as it is drawn into the aperture of the outer tube. The cutting action is obtained when the squared, sharp edge of the blade passes over the sharp lower edge of the aperture in the outer needle.

The present invention involves an improved cutting apparatus which is more efficient, provides a more consistent and complete contact of the two cutting surfaces, and retains the sharpness of the cutting edges for a longer period of time.

It is an object of the present invention to provide a more efficient microsurgical vitrectomy probe for the removal of the vitreous.

It is another object of the present invention to provide an improved needle and blade mechanism for a vitrectomy probe.

It is a further object of the present invention to provide an improved cutting blade for a microsurgical vitrectomy probe.

Other objects, features and advantages of the present invention will become apparent from the subsequent description and the appended claims taken in conjunction with the accompanying drawings.

DESCRIPTION OF THE DRAWINGS

FIG. 1 is a side view of a microsurgical probe;

FIG. 2 is a cross-sectional view of the probe of FIG. 1;

FIG. 3 is an enlarged cross-sectional view of the needle and blade mechanism of the probe of FIGS. 1 and 2;

FIG. 4 is a top view of the blade end of the inner hollow tubular member of FIGS. 2 and 3;

FIG. 5 is a cross-sectional view of the blade of FIG. 4 taken along the line 5—5 in FIG. 4;

FIG. 6 is a plan view of the suction and cutting aperture in the end of the needle probe; and FIG. 7 is an exaggerated cross-sectional view of the needle and blade mechanism taken along the line 7—7 in FIG. 3.

DETAILED DESCRIPTION OF THE PREFERRED EMBODIMENT

Referring to various Figures of the drawing, wherein like reference characters refer to like parts, there is shown generally at 10 in FIG. 1 a vitrectomy probe for use in ophthalmic surgical applications. The probe shown in FIG. 1 is suitable for use with compatible microsurgery systems known in the art and is adapted to be disposable after one complete surgical operation.

The probe 10 generally comprises a housing 12 from which extend a suction outlet port 16, an fluid inlet port 22, and a probe needle 18 containing a vitreous inlet aperture or port 20. A fluid inlet tube 23 connects the fluid inlet port 22 to a pressurized fluid supply (not shown). The housing 12 may be constructed from a polysulfone resin and comprises a fingergrip portion 24, a nose 28 which contains air vents 30, and a cap 26.

As is shown in more detail in FIG. 2, the probe 10 supports the outer probe needle 18 in the front (nose) 28 of the housing 12. The probe needle may be a T304 stainless steel needle, 500 polish; this needle has been found to have a sufficiently smooth interior bore. Inserted within the probe needle 18 is a hollow inner tubular member 32 which extends into the fingergrip portion of the housing 12. A cutting blade 36 is located on the outer end of the tubular member 32. The tubular member is attached to the end of the suction outlet tube 16 by any conventional means 34, such as crimping, brazing, or the like. The entire blade, inner tubular member and suction outlet tube assembly is reciprocable such that the blade 36 may be slid across the port 20 in the outer needle 18. The blade, tubular member and suction outlet assembly are automatically returned by the spring means 38 to an open position whereby the port 20 is open. The spring is preferably a 1/32 diameter stainless steel wire compression spring. The spring 38 is contained within the housing of the probe and is supported by a polysulfone O-ring retainer 40 and acts upon a flanged collar retainer 42 through which has been inserted the inner tubular member and suction outlet tube assembly.

The length of the cutting motion is limited by an aluminum stop washer 44 which contacts the retainer 42 at the end of the cutting stroke. The housing 12 is divided by a diaphragm 46 into a spring chamber 39 and a fluid chamber 47. The diaghragm 46 abuts against the diaphragm stop 48 which fits over the inwardly extending flange 50 of the cap 26 when the blade and suction outlet are in the open position.

The fluid chamber 47 is sealed substantially fluid-tight by an O-ring 52. The fluid inlet port 22 is connected to a controlled supply of a pressurized fluid (not shown) through inlet tube 23. The cap 26 contains a groove 54 along its outer rim 56 which interlocks with ridge 58 on the inner portion of the outer rim 60 of the housing 12. The outer tubular needle 18 is sealed by an O-ring 62.

The inner tubular member 32 and suction tube 16 are reciprocated by injecting a pulsating pressurized fluid such as air through the fluid inlet tube 23 and the fluid inlet port 22 into the fluid chamber 47. The pulses of increased pressure in the fluid chamber 47 cause the diaphragm 46 to push against the retainer 42 which is connected to the suction tube 16. The retainer 42 and suction tube 16 are urged away from the fluid chamber 47 toward the stop ring 44, causing the spring 38 to be compressed and the inner tubular member 32 and blade 36 to slide toward the cutting position. When the pressure in the fluid chamber is reduced or released, the spring means 38 forces the retainer 42, the suction tube 16 and hence the blade 36 to the open position. The pressurized air source supplies air under pressure alternately between atmospheric to 30 p.s.i. approximately every 20 milliseconds. With an adjustable control mechanism, the cutting blade 36 can cycle from 0–600 cutting strokes per minute (0–10 strokes per second).

It is preferable that the inner bore of the outer needle 18 be as smooth as possible. This has at least three primary advantages. First, the amount of friction between the cutting blade and the outer needle is greatly reduced which increases the reaction time of the cutting cycle and reduces the forces on the reciprocating means, particularly the driving diaphragm and the return spring. Second, a smooth inner diameter reduces the abrasive action on the cutting blade and prolongs the life of the cutting edge of the cutting blade. A dull blade causes a pulling effect rather than the shearing effect when reciprocated over the cutting edge of the outer needle. Third, the smoother the inner diameter near the cutting edge of the outer needle, the closer the cutting blade will pass to the cutting edge of the outer needle. Any roughness near the edge of the cutting edge of the outer needle will cause spacing between the two cutting edges and will reduce the effectiveness of the shearing action.

The outer end 19 of the outer needle 18 may be closed and hermetically sealed by various methods known in the art. For example, the end 19 can be swedged or roll closed. This is effective, but causes the tip or end 19 to be rounded which in turn causes the port 20 to be positioned further from the end. Another more preferable manner of sealing the end 19 is to arc weld the end closed using a plasma arc. This causes the end to melt into itself leaving a rounded "ball" of metal which seals the end. The "ball" may be worked to form a blunter or more square end (as shown in FIGS. 2 and 3) which allows the port 20 to be closer to the end. The arc welding also leaves a slight radius 21 of material on the inside of the end 19, but this does not affect the operation of the probe as the radius 21 fits inside the open end of the inner cutting tube or blade 36.

The shape of the cutting blade 36, the outer end of the reciprocating inner tubular member 32, and the vitreous inlet port 20 are all important. FIGS. 3–7 illustrate the shapes of these features as well as the inventive cutting mechanism. As the blade 36 is reciprocated across the port 20, the cutting edge 37 of the blade 36 will slide across the outer or cutting edge 64 of the outer needle 18. The cutting edge 37 should be square; i.e. the cutting end of the inner tubular member 32 should be substantially perpendicular to its longitudinal axis.

Also, the cutting edge 64 of the aperture 20 is beveled or curved slightly toward the inner diameter cutting edge 65 to supply a clean entrance for the insertion of vitreous into the aperture 20 and an improved cutting action. Moreover, the inner edge 66 of the port is preferably concave away from the cutting edge 64 (as best shown in FIG. 6) so that the blade 36 will be supported by the sides of the edge 66 as it is guided toward and over the cutting edge 64. The opposing edge 66 is also beveled (as shown in FIG. 3) to allow the entrance of the vitreous fibers into the port 20 to be viewed more easily by the surgeon.

The curvature of the cutting edge 64 may be formed simultaneous to the formation of the port 20. As illustrated in FIG. 3, a spherical drilling or grinding tool may be used to form the port 20 leaving a curved portion 64. The radius R in FIG. 3 illustrates this relationship.

Preferably, the radius R of the cut is about 0.010 inches. Also, the outer diameter of the outer needle 18 is 0.0355 inches and the thickness of the tubular wall is 0.005 inches. The opposing edge 66 may then be beveled to finish the formation of the vitreous inlet port 20. A bevel of approximately 60 degrees has been found to provide optimal visual access.

As indicated, the edge 66 should be rounded to allow the blade 36 to be supported or guided along its cutting edge 37 for as long as possible. The preferred shape of the aperture or port 20 is shown in FIGS. 3 and 6. Minimizing the distance that the blade 36 will not be supported and could dip slightly, reduces the chances that the blade 36 will impact the cutting edge 65 of the outer needle rather than sliding smoothly across it. If the inner needle abuts into the edge 65, the shearing effect will not take place and the probe will not cut effectively. Any impacting of the cutting edges will reduce the cutting efficiency of that particular stroke and also dull each of the cutting edges 37 and 65.

FIG. 4 illustrates the end of the inner hollow tubular member 32 and the blade 36. A slot or notch 68 is cut into the blade 36 on the side opposite the cutting edge 37. The blade is then flared at the end into an elliptical shape as is illustrated in FIGS. 5 and 7. The slot or notch 68 can be cut with a small rotating saw or the like, which will leave a small run-out 69. The blade 36 is flared into an elliptical shape with a mandrel which is inserted in the open end of the cutting blade tubular member. The tube is formed or pressed in place around the mandrel. Thus, the cutting edge 37 of the blade 36 is slightly less rounded across the aperture 20 and will provide a more even cut along the length of the cutting edge 65 when the blade is inserted in the outer hollow tube 18.

A key factor in providing a consistent shearing cut is the configuration of the cutting blade 36. As indicated, the cutting blade 36 is configured by slitting the end of the inner tubular member 32 and flaring it into an elliptical shape. The shape of the flare of the cutting blade is important in increasing the performance of the cutting blade. When the cutting blade is flared into an elliptical shape rather than leaving it in a round or circular shape, the cutting edge 37 will tend to be flatter along the edges of the cutting edge 65 of the outer needle. If the cutting edge 37 was round, the cutting action would be localized in the center of the cutting edge 65, rather than spread out evenly along its length.

Moreover, the amount of flaring induced to the end of the cutting blade is important. By forming the end of the cutting tube or blade 36 into an elliptical shape, the blade 36 will attempt to regain and retain that shape after it is inserted into the outer tube 18. Since there is only a few thousandths difference in diameters of the mating tubular members, the force created by the inner tubular member attempting to form an elliptical shape inside a round tube will cause the cutting edge 37 of the blade 36 to precisely take the round cross-section of the corresponding part of the outer tube, i.e. across the inlet port 20, causing a tight shearing action. In this regard, sufficient expansion in the elliptical direction is necessary to achieve a spring tension to hold the cutting blade into substantial conformity with the inner diameter of the outer needle, but excessive spread will cause excessive spring tension. The spring tension results from the compression experienced by the tubular blade 36 when it is installed in the outer tube 18 after the blade 36 has been flared. Excessive spring tension will increase the friction force during reciprocation which will increase the load on the reciprocation means and tend to dull the blade. Further, too great of an expansion of the blade 36 during formation of the elliptical shape could exceed the elastic deformation range of the tubular material and the spring force might be lost altogether.

The inner diameter of the outer tubular needle member 18 is 0.0255 inches, within a 0.0005 inch tolerance. The outer diameter of the inner tubular member is typically 0.0250 inches, within a 0.0005 inch tolerance. It has been found through experimentation that the blade end 36 of the inner tubular member should be flared such that the largest outer dimension, along the major axis of the ellipse, should be 0.0295 inches, within a 0.001 inch tolerance, before insertion into the outer tube. Thus, the outer dimension of the blade 36 should be approximately 111% to 125% of the inner diameter of the outer needle prior to insertion therein. The dimension of the minor axis of the elliptically shaped blade 36 is approximately 0.024 inches.

As is best illustrated in FIGS. 5 and 7, the elliptical flaring of the blade 36 provides a less curved cutting surface 37. The edges of the slot 68 may curve inwardly (exaggerated in FIG. 7 for purposes of illustration) under the compressive force resulting from insertion of the flared blade 36 into the outer tubular member 18.

While it will be apparent that the preferred embodiments of the invention disclosed are well calculated to fulfill the objects, benefits, or advantages of the invention, it will be appreciated that the invention is susceptible to modification, variation and change without departing from the proper scope or fair meaning of the subjoined claims.

What is claimed is

1. A microsurgical cutting device for cutting and removing fibrous gel, comprising a housing, a substantially hollow outer needle having an outward end with an aperture therein, a cutting blade disposed within said outer needle, actuation means, and suction means;

said housing containing a spring compartment and containing means for communicating with said actuation means, said spring compartment containing a compression spring acting against said actuation means;

said outer needle extending outwardly from said housing and containing a hollow tubular member reciprocable within said outer needle, said hollow tubular member communicating with said suction means and having said cutting blade extending toward said apertured end of said outer needle;

said inner tubular member being reciprocable within said outer needle between a first open position and a second cutting position wherein said cutting blade slides across said apertured end of said outer needle, said actuation means tending to force said inner tubular member and cutting blade toward said second position and said compression spring tending to restore said inner tubular member and cutting blade to said first position;

said aperture in said outer needle having a cutting edge and a radially rounded leading edge opposing said cutting edge, said cutting edge having an axially inwardly curved surface and said opposing edge having a surface inwardly beveled toward said cutting edge; and wherein said actuation means comprises a sealed fluid compartment in said housing and communicating with a pressurized fluid source and a diaphragm, said fluid compartment separated from said spring compartment by said diaphragm, said diaphragm urging said tubular member toward said second position when pressurized fluid is injected into said fluid chamber.

2. The invention according to claim 1 wherein said outer needle has a substantially smooth, uniform inner surface.

3. The invention according to claim 1 wherein said blade is axially outwardly flared.

4. The invention according to claim 1 wherein said blade is elliptically configured prior to insertion into said outer needle.

5. An improved microsurgical cutting device supported by, extending from and adapted for use with a surgical probe having reciprocating means and suction means, said cutting device comprising:
a hollow outer needle operatingly connected to said suction means and having an apertured receiving end, said outer needle having a substantially smooth, uniform inner diameter; and
a substantially cylindrical inner member reciprocable within said outer needle, having a cutting end disposed within said outer needle and having an opposite end operatingly connected to said reciprocating means, said cutting end substantially conforming to the inner diameter of said receiving end and said cutting end being outwardly flared and elliptically deformed from a circular configuration such that at least one cutting edge is formed at the cutting end which has a decreasing radius of curvature from the center of said edge prior to insertion of said inner member into said outer needle.

6. The invention according to claim 5 wherein said apertured outer needle has a cutting aperture edge and a rounded leading aperture edge opposing said cutting edge.

7. The invention according to claim 5 wherein said apertured outer needle has an axially inwardly beveled cutting aperture edge and an opposing aperture edge beveled inwardly toward said cutting edge.

8. An improved microsurgical cutting blade for use with a surgical probe having a reciprocable blade holding actuation means, suction means and an outer probe needle having a smooth, uniform inner diameter and at least one cutting edge wherein:
said blade is substantially tubular and is reciprocable within and substantially conforms to the inner diameter of said probe needle;
said blade has a first end disposed within and supported by said blade holding means and is operatingly connected to said suction means; and
said blade has a preformed flared cutting end having a predetermined degree of flexibility said cutting end receiving a compressive force from said probe needle and said cutting end providing a corresponding tension force, said tension force tending to force said flared end against said probe needle and increasing the efficiency of the shearing effect of reciprocating said blade past said cutting edge of said probe needle.

9. The invention according to claim 8 wherein:
said blade has a notch beginning at the cutting edge of said blade and extending into said blade; and
said cutting end of said blade prior to insertion in said probe needle is expanded into an elliptical "C" shaped configuration having a major and minor axis, such that the outer diameter of said blade along said major axis is greater than the inner diameter of said outer tube.

10. The invention of claim 9 wherein the cutting end is expanded prior to insertion into said probe needle such that the outer dimension of said blade along said major axis is between 111% and 125% of the inner diameter of said outer tube.

11. The invention according to claim 8 wherein said outer needle has a substantially smooth, uniform bore.

12. The invention according to claim 8 wherein said cutting end of said blade is elliptically configured prior to insertion into said outer needle.

13. A microsurgical cutting device for cutting and removing fibrous gel, comprising a fingergrip, a substantially hollow outer needle having an open end disposed within said fingergrip and a substantially closed end extending from said fingergrip, a reciprocable tubular tool having a cutting end disposed within said needle, said cutting end having a preformed outwardly flared and elliptical transverse configuration, means for reciprocating said tool operatingly connected to said tool, a suction means connected to the end of said tool opposite said cutting end; and
said closed end of said needle having an inlet aperture, said cutting end having an outer diameter substantially conforming to the inner diameter of said needle in the vicinity of said inlet aperture and said cutting end being forced into close conformity within said inner diameter of said needle by a spring force resulting from compressive forces acting between said needle and said cutting end.

14. The invention according to claim 13 wherein said aperture has a cutting slot edge and a rounded leading slot edge opposing said cutting edge.

15. The invention according to claim 13 wherein said aperture has an axially inwardly curving cutting slot edge and an opposing slot edge beveled inwardly toward said cutting edge.

16. The invention according to claim 13 wherein said outer needle has a substantially smooth, uniform bore.

* * * * *